United States Patent [19]
Tritsch et al.

[11] Patent Number: 6,071,963
[45] Date of Patent: *Jun. 6, 2000

[54] WATER DISPERSIBLE COMPOSITIONS

[75] Inventors: Jean-Claude Tritsch, Saint-Louis, France; Johann Ulm, Oberwil, Switzerland

[73] Assignee: Roche Vitamins Inc., Parsippany, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/946,480

[22] Filed: Oct. 7, 1997

[30] Foreign Application Priority Data

Nov. 6, 1996 [CH] Switzerland ............... 2741/96

[51] Int. Cl.$^7$ .................................................. A61K 31/20
[52] U.S. Cl. ............................ 514/560; 514/801
[58] Field of Search ....................... 514/560, 801

[56] References Cited

U.S. PATENT DOCUMENTS 5,478,569  12/1995  Berneis et al. .

FOREIGN PATENT DOCUMENTS 2513517   4/1983   France .
96/20612  7/1996   WIPO .
96/26647  9/1996   WIPO .

OTHER PUBLICATIONS

Abstract of Japanese Patent #5078692, Mar. 30, 1993.
Abstract of Japanese Patent #60037934, Feb. 27, 1985.
Abstract of Japanese Patent #3161448, Jul. 1, 1991.
Abstract of Japanese Patent #3263499, Nov. 22, 1991.
Abstract of German Patent DE 3603000 A1, Jan. 30, 1987.
Merck Index, #787, p. 112, 1983.
Brühl et al., "Triglyceride mit mehrfach ungesättigten Fettsäuren in Muttermilch und in Rohstoffen für Säuglingsnahrung", Fat Sci. Technol., vol. 96, Nr. 6, pp. 223–227 (1994).

*Primary Examiner*—Rebecca Cook
*Attorney, Agent, or Firm*—Mark E. Waddell; Stephen M. Haracz; Bryan Cave LLP

[57] ABSTRACT

Novel, stable, cold water dispersible preparations of fat-soluble substances contain a microbially produced oil rich in arachidonic acid. These preparations are manufactured by preparing an aqueous emulsion of the microbially produced oil which has been stabilized with an antioxidant and fish gelatin and if desired converting this emulsion into a dry powder. The preparations in accordance with the invention can be used for human nutrition.

19 Claims, No Drawings

WATER DISPERSIBLE COMPOSITIONS

BACKGROUND OF THE INVENTION

The present invention is concerned with novel, stable, cold water-dispersible pulverous preparations of a microbially produced oil, referred to hereinafter as SCO (Single Cell Oil), which is rich in Arachidonic Acid, referred to hereinafter as AA, as well as a process for their manufacture.

Cold water-dispersible preparations of fat-soluble substances play an important role in the field of human nutrition. Such preparations are usually commercialized in the form of emulsions or dry powders because of the water-insolubility of the fat-soluble active ingredients and the fact that they have a more or less pronounced instability and are difficult to handle. It is common in such preparations that the active ingredients, i.e. the fat-soluble substances, are generally enveloped by means of a matrix component. This matrix component is responsible, inter alia, for the protection of the active ingredient or for its stabilization, for an optimal resorption and for the water-dispersibility of the final preparation which may be required.

SUMMARY OF THE INVENTION

In accordance with the invention it has now been found that a preparation of the SCO referred to earlier, which is especially stable and which can be handled well, can be manufactured when fish gelatine is used as the protective colloid and an antioxidant is added.

DETAILED DESCRIPTION

The stable, cold water-dispersible preparations of fat soluble substances provided by the invention accordingly contain fish gelatin as the matrix component and an antioxidant as a stabilizer.

Antioxidants which are used are:

a) for the oil phase: tocopherol, an ascorbic acid ester or a mixture of an ascorbic acid ester and tocopherol, with the ascorbic acid ester being preferably ascorbyl palmitate;

b) for the aqueous phase: alkali or alkaline earth salts of ascorbic acid, preferably Na ascorbate.

The gelatine available under the name "Norland HiPure Fish Gelatin" from the firm Norland Products Inc., 695 Joyce Kilmer Ave., New Brunswick, N.J., USA, is an especially preferred fish gelatine.

Any tocopherol can be used in the present invention, with examples of such tocopherols being α-tocopherol, γ-tocopherol or a mixture of natural tocopherols. In a preferred embodiment a mixture of natural tocopherols is used.

The ascorbyl palmitate and tocopherol are preferably used in a ratio of 1:5 to 1:25, especially 1:5, and the total amount which is added to the SCO is advantageously 1200–5250 parts per million, especially 1200–2000, preferably about 1200 parts per million. The ascorbyl palmitate and tocopherol can be added as a mixture or individually. When tocopherol is used alone, then the total amount is advantageously 1000–5000 parts per million, especially 1000–2000, preferably about 1000, parts per million.

The preparations in accordance with the invention can be manufactured in principle by preparing an aqueous emulsion of the SCO and the fish gelatine and converting this emulsion into a dry powder. This manufacturing process represents a further object of the present invention.

As a rule, the fish gelatine, and optionally adjuvants are firstly dissolved in water, which is conveniently accelerated by vigorous stirring. If desired, an antioxidant, for example Na ascorbate, can be added to the aqueous phase.

Usual adjuvants are, for example, mono- and di-saccharides; sugar alcohols; starch derivatives, e.g. maltodextrin; milk proteins, e.g. sodium caseinate; as well as plant proteins, e.g. soya protein, potato protein and wheat protein. Moreover, it has been found to be advantageous to carry out the dissolution of the fish gelatine at room temperature or elevated temperature, especially in the temperature range of 20° C. to 90° C., preferably 50° C. to 70° C. The so-called matrix is obtained in this manner. Then, the SCO stabilized by an antioxidant is emulsified in this matrix, advantageously by homogenization at atmospheric pressure or elevated pressure up to 1000 bar (100 MPa), preferably at 300–500 bar (30–50 MPa), or also using ultrasonics or similar technology. The pressure and the temperature are not critical parameters in this procedure, which can be carried out readily at temperatures of about room temperature to about 70° C., especially between about 60° C. and 70° C., and atmospheric pressure.

The weight ratio of SCO to the other components (fish gelatine, sugar etc.) present in the final product is usually about 20:80 to about 80:20, with the precise ratio depending on the respective biological requirement of AA and on the need for a homogeneous and sufficiently fine distribution of the final preparations in the forms of application which are proposed for consumption.

The conversion of a thus-produced emulsion, which generally contains about 20 to about 80 weight percent of SCO depending on ingredients, into a dry powder can be effected e.g. by spray drying, the double dispersion process or also the starch catch process. In the latter process the sprayed emulsion droplets are caught in a starch bed and subsequently dried. Where required, the emulsion to be sprayed can be diluted with water.

In general, the preparations in accordance with the invention have a good cold water-dispersibility as well as a good flowability.

The preparations in accordance with the invention can be used for human nutrition, especially that of neonates.

The present invention is illustrated by the following Examples.

EXAMPLE 1

48.5 g of dried fish gelatine and 48.5 g of crystalline sugar were placed in a 600 ml glass beaker. Then, 80 ml of deionized water were added and the mixture was brought into solution at 50° C. while stirring with a mincer disc (1000 r/min.). Thereupon, 60 g of a SCO containing 50% AA, which had been stabilized with a mixture of 1000 ppm of a mixture of natural tocopherols and 200 ppm of acorbyl palmitate, was emulsified into this matrix and stirred for 15 minutes (during the emulsification and subsequent stirring the speed of the mincer disc was 4800 r/min.). After this time the internal phase of the emulsion has an average particle size of about 200 nm. The emulsion was then diluted with 90 ml of deionized water and heated to 65° C. 1 kg of starch fluidized with silicic acid was then placed in a laboratory spray tank and cooled to about 5° C. The emulsion was then sprayed into this using a rotating spray nozzle. The thus-obtained particles enveloped with starch were then sieved off from the excess starch and dried at room temperature using compressed air. There were obtained about 190 g of dry powder with an AA content of 17.4%.

EXAMPLE 2

44.2 g of dried fish gelatine, 44.2 g of crystalline sugar and 8.6 g of sodium ascorbate were placed in a 600 ml glass beaker. Further processing was carried out analogously to Example 1.

The average particle size of the internal phase was 180 nm. About 190 g of dry powder with an AA content of 17% were obtained.

What is claimed is:

1. A stable water-dispersible dry pulverous composition prepared by drying an emulsion comprising:
   a) about 20 to about 80 weight percent of a microbially produced oil, the oil comprising,
      i) arachidonic acid and
      ii) a first antioxidant,
   wherein the oil is emulsified in a matrix, the matrix comprising fish gelatin that is present in an amount sufficient to render the oil dispersible in water and
   b) a second antioxidant for the aqueous phase that is selected from the group consisting of an alkali earth salt of ascorbic acid and an alkaline earth salt of ascorbic acid.

2. A method for the manufacture of a stable water-dispersible dry pulverous composition comprising (A) about 20 to about 80 weight percent of a microbially produced oil, the oil comprising: (i) arachidonic acid and (ii) a first antioxidant, wherein the oil is emulsified in a matrix, the matrix comprising fish gelatin that is present in an amount sufficient to render the oil dispersible in water; and (B) a second antioxidant for the aqueous phase that is selected from the group consisting of an alkali earth salt of ascorbic acid and an alkaline earth salt of ascorbic acid, the method comprising the steps of:
   (a) dissolving fish gelatin together with a second antioxidant in water to form an aqueous matrix;
   (b) emulsifying the microbially produced oil in the aqueous matrix of step (a) to form an emulsion; and
   (c) converting the emulsion of step (b) into a powder by spray drying.

3. The composition of claim 1 further comprising an adjuvant.

4. The composition of claim 1 wherein the antioxidant is selected from the group consisting of tocopherol and ascorbic acid ester, on a mixture thereof.

5. The composition of claim 4 wherein the antioxidant is a mixture of natural tocopherols.

6. The composition of claim 4 wherein the antioxidant is a mixture of ascorbic acid ester and tocopherol.

7. The composition of claim 6 wherein the ascorbic acid ester is ascorbyl palmitate.

8. The composition of claim 7 wherein the ascorbyl palmitate and tocopherol are present in a ratio of from 1:5 to 1:25.

9. The composition of claim 8 wherein the ratio is 1:5.

10. The composition of claim 6 wherein the total amount of ascorbyl palmitate and tocopherol is from about 1200 to about 5250 parts per million.

11. The composition of claim 10 wherein the total amount of ascorbyl palmitate and tocopherol is from about 1200 to about 2000 parts per million.

12. The composition of claim 11 wherein the total amount of ascorbyl palmitate and tocopherol is from about 1200 parts per million.

13. The composition of claim 4 wherein the antioxidant is tocopherol which is present in an amount of from about 1000 to about 5000 parts per million.

14. The composition of claim 13 wherein the total amount of tocopherol is from about 1000 to about 2000 parts per million.

15. The composition of claim 12 wherein the total amount of tocopherol is about 1000 parts per million.

16. The method of claim 2, wherein the first antioxidant is selected from the group consisting of tocopherol and an ascorbic acid ester or a mixture of an ascorbic acid ester and tocopherol.

17. The method of claim 2 further comprising adding an adjuvant to the aqueous matrix of step (a).

18. The method of claim 2 further comprising adding an second antioxidant to the aqueous matrix of step (a).

19. The method of claim 18 wherein the antioxidant is sodium ascorbate.

* * * * *

UNITED STATES PATENT AND TRADEMARK OFFICE
CERTIFICATE OF CORRECTION

PATENT NO : 6,071,963

DATED : June 6, 2000

INVENTOR(S) : Jean-Claude TRITSCH

It is certified that error appears in the above-identified patent and that said Letters Patent are hereby corrected as shown below:

Column 3, line 40, change "on" to --or--;

On the title page, under "OTHER PUBLICATIONS," the following references should be listed:

Norland Products, Inc. - Res. Discl., 284, 788 (abstract) (1987);

Berneis, et al., EPA 89-110871 (abstract) (1989); and

Bruehl, et al., Fett Wiss. Technol., 96(6) 223-227 (abstract) (1994).

Signed and Sealed this

Third Day of April, 2001

*Attest:*

NICHOLAS P. GODICI

*Attesting Officer*     *Acting Director of the United States Patent and Trademark Office*